United States Patent
Tsadka

(10) Patent No.: US 6,208,750 B1
(45) Date of Patent: Mar. 27, 2001

(54) METHOD FOR DETECTING PARTICLES USING ILLUMINATION WITH SEVERAL WAVELENGTHS

(75) Inventor: Sagie Tsadka, Yavne (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/110,868

(22) Filed: Jul. 7, 1998

(51) Int. Cl.$^7$ ........................................ G06K 9/00
(52) U.S. Cl. .................. 382/145; 250/559.18; 348/125; 356/237.4; 356/239.8
(58) Field of Search ........................... 382/141–145, 382/147–150, 152; 356/237.4, 239.8, 71; 350/71; 250/271, 222.2, 227.23, 492.1, 492.2, 494.1, 495.1, 503.1, 559.11, 559.4, 559.41, 559.44, 559.45, 578.1; 348/125, 126, 128, 131

(56) References Cited

U.S. PATENT DOCUMENTS

| 4,731,855 | 3/1988 | Suda et al. | 382/8 |
| 5,072,128 | * 12/1991 | Hayano et al. | 250/559.18 |
| 5,539,514 | * 7/1996 | Shishido et al. | 356/237 |
| 5,699,447 | 12/1997 | Alumot et al. | 382/145 |

\* cited by examiner

*Primary Examiner*—Bhavesh Mehta
(74) *Attorney, Agent, or Firm*—Sughrue, Mion, Zinn, Macpeak & Seas, PLLC

(57) ABSTRACT

A process is provided for detecting small particles on wafer surfaces by irradiating the wafer surface with two light beams having a small difference in wavelength, collecting the light scattered by the wafer in at least one direction, separating the collected light into two component beams having the wavelengths of the irradiating beams, and comparing the intensities of the two component beams. The intensities of the component beams are transduced to digital signals which are fed to a comparator. An apparatus is also provided which comprises a stage for supporting a wafer, laser source and optics for generating two laser beams having different wavelengths, superimposing them and scanning the wafer with them, a sensor for sensing the light scattered by the wafer and separating it into two components having the said wavelengths, an A/D converter for generating digital signals corresponding to said components and a comparator for analyzing whether said signals indicate the presence of small particles.

25 Claims, 2 Drawing Sheets

METHOD FOR DETECTING PARTICLES USING ILLUMINATION WITH SEVERAL WAVELENGTHS

FIELD OF THE INVENTION

This invention relates to a method and apparatus for the detection of very small particles on patterned or bare surfaces, particularly of semiconductor wafers.

BACKGROUND OF THE INVENTION

Bare, as well as patterned, semiconductor wafers are checked for the presence of defects, particularly for the presence of particles. Prior art methods and devices are used in order to detect foreign substances in patterned wafers.

One method comprises scanning the wafer surface with a laser beam and analyzing the number and direction of diffraction lights, produced by the pattern edges, by means of a plurality of light detection cells arranged cylindrically. Other methods involve using polarized light, or comparing an inspected pattern with an ideal pattern, or analyzing the light reflected from a wafer surface by distinguishing between normal directions and abnormal directions due to reflection from particles, or employing a planar array of individually addressable light valves for use as a spatial filter in an imaged Fourier plane of a diffraction pattern.

U.S. Pat. No. 4,731,855 includes in its Background of the Invention a list of various methods for performing semiconductor wafer inspections, and said list is incorporated herein by reference.

The methods and apparatus of the prior art have several drawbacks, partly discussed in the cited references, such as errors due to faulty registration and other causes, false alarms consisting in the detection of defects that are only apparent, and so on. All of them, further, have the common defect of requiring complex apparatus, with high mechanical precision, and requiring long operation times and having therefore a low throughput.

In order to overcome the disadvantages of the prior art, the applicant has invented a method and an apparatus that are described and claimed in a copending patent application, Ser. No. 09/110,870 filed concurrently with this application, the contents of which are entirely incorporated herein by reference. The prior art methods do not permit the identification of particles having extremely small dimensions, particularly smaller than the width of the pattern lines, e.g. sub-micron particles. Such identification is difficult even with the method and apparatus of the aforesaid copending application. Modern wafers have pattern widths in the order of 0.18–0.5 $\mu$m. Particles having smaller sizes, e.g. a size of about 0.1–0.2 $\mu$m, are particularly difficult to detect. Their detection is difficult on uniform surfaces, such as those of unpatterned wafers or memory areas of patterned wafers, as well.

It is therefore a purpose of this invention to permit the detection of such particles.

It is another a purpose of this invention to permit the detection of such particles in each pixel of the controlled surface, without reference to its pattern and without comparing patterns.

It is a further purpose of this invention to provide a high speed detection method which has a very high throughput and permits the on-line detection of sub-micron particles.

It is a still further purpose of this invention to provide a detection method that is compatible with the method that forms an object of the aforesaid copending application and can be carried out concurrently with it.

It is a still further purpose of this invention to provide an apparatus for the detection of sub-micron particles.

It is a still further purpose of this invention to provide an apparatus that can be combined with the apparatus that forms an object of the aforesaid copending application, to form a single unit.

Other purposes and advantages of the invention will appear as the description proceeds.

SUMMARY OF THE INVENTION

This invention comprises a process for detecting small particles of foreign matter on a surface, particularly a patterned or bare surface of a semiconductor wafer, which comprises:

I—irradiating the surface with two light, generally laser, beams, that are identical in all their parameters, but have a small difference in wavelength;
II—collecting the light that is scattered by the surface in at least one direction, preferably by means of optical fibers,
III—separating the collected light by filtering it in two component beams, each of which has the wavelengths of one of the irradiating beams; and
IV—comparing the intensities of said two component beams.

Preferably, the scattered light is collected in a plurality of directions and the intensities of said two component beams are compared in each of them. However, one direction is chosen for processing the signals generated in it, as hereinafter described, and the signals generated in other directions are neglected. The direction chosen is one in which the intensity of the two component beams is not too high.

By "small particles" is meant herein particles that have dimensions much smaller than the wavelengths of the illuminating laser beams, especially particles having dimensions in the order of a few tenths of a micron (hereinafter "sub-micron" particles). The "parameters" of the laser beams, as this term is used herein, comprise every physical and geometric features of the laser beams, such as polarization, size and shape of their footprints or light spots on the irradiated surface, angle of illumination, etc. The laser beams are preferably, though not necessarily, at a slant with respect to the wafer surface. Slanting the beams causes the wafer surface to be seen as flatter than it would if the beam were perpendicular to it, which is advantageous from the processing viewpoint. They may have superimposed or adjacent footprints, as will be better explained hereinafter.

While pattern lines may scatter light with different intensity depending on the wavelengths, or in other words produce scatter signals having different intensities when they are irradiated with light beams having different wavelengths, such intensity differences are much smaller than those of the light scattered by small particles. Therefore a marked difference in the intensities of the aforesaid two component beams is the index of the existence of the small particle. Said intensity difference is preferably determined by directing each component onto a photodetector, thereby producing an optical signal, transducing the optical signal into an analog electric signal, sampling the two electric signals, and feeding the resulting digital signal to hardware or software comparing means.

Before comparing the intensities of the two component beams, they will be preferably amplified, and, if desired, shaped. A threshold intensity may be established, below which the signals will be considered as noise and therefore irrelevant, and will not be further processed.

In order to obtain two laser beams, having a similar geometry and the same intensity but a small difference in wavelength, two laser beams of the desired wavelength can be generated, and then imparted the desired similar geometry and focused on the surface under examination by optical means, which may include mirrors, beam splitters, lenses and the like.

The difference in the wavelengths of the two irradiating beams should be small, preferably between 1 and 5% of the average of the two wavelengths. The average wavelength of the two beams is not critical. By way of example, the two beams may have wavelengths of 630 nm and 670 nm, respectively.

The intensity difference of the collected light components, having the two wavelengths of the irradiating beam, is normalized by means of the sum of the intensities of the two components. If the two components have intensities ($\alpha 1$ and $\alpha 2$, the normalized difference of the intensities is given by $(\alpha 1-\alpha 2)/(\alpha 1+\alpha 2)$. To be considered significant, for the purpose of this invention, the normalized difference of intensities must be above a threshold, which is between 5 and 100%.

In the aforementioned copending application, a method and an apparatus for the analysis of surfaces, particularly for the detection of particles of patterned semiconductor wafers, are described and claimed. The method comprises checking all parts of the pixels of the surface under control, and detecting suspected pixels by a) successively scanning the individual pixels by mean of at least one scanning light beam, b) determining the signature of each pixel, representing the way in which the pixels scatters the light of a scanning beam, and c) determining whether such signature has the characteristics of a signature of a defective pixel.

The apparatus according to the preferred embodiment this invention is similar to the aforementioned apparatus from the mechanical viewpoint, viz. comprises the same means for supporting and rotating the wafer and varying the distance of the spot of the irradiating beams from the wafer center, and optical means for collecting the light scattered by the wafer, though not necessarily in a number of directions, but in at least one direction. It differs from said aforementioned apparatus in that it comprises means for generating at least two irradiating laser beams, equal except for having different wavelengths, and for directing them onto the wafer, preferably at a slant; and means, e.g. filter means, for separating the scattered light collected into two component beams having the wavelengths of the two irradiating laser beams. The means for processing each of the two component beams—optical signals—so separated comprise photoelectric means for transducing the optical signals to electric analog signals, amplifying means, if desired, means for sampling each analog signal at a high sampling frequency, e.g. 20 MHz, and means for comparing the samples representing the two component beams, to determine whether their difference indicates the presence of a small foreign particle.

Therefore, this invention provides an apparatus for the detection of small particles on surfaces, particularly surfaces of patterned, semiconductor wafers, which comprises:
a) a stage for supporting a wafer;
b) laser source and optics for generating at least two laser beams having different wavelengths;
c) optical components for superimposing said beams and directing them onto the wafer to scan the wafer;
c) a sensor for sensing the scattered light reflected by the wafer and separating it into two components having the wavelengths of the said laser beams;
d) A/D converter for generating digital signals corresponding to said two components; and
e) a comparator for analyzing whether said digital signals indicate the presence of small particles.

The apparatus optionally further comprises means for associating to each detected particle its coordinates on the wafer.

In a preferred embodiment of the invention said stage for supporting the wafer is a turntable and said optical components direct the superimposed laser beams across a straight or curved line over the surface of the wafer to scan the same as it is rotated. This manner of scanning can be called "polar scanning" and the coordinates of the detected particles are polar coordinates. In another embodiment said stage is a slide, viz. a support that displaces the wafer along a first line, and said optical components direct the superimposed laser beams over the surface of the wafer along another line, to scan the wafer surface. If the said two lines are straight lines perpendicular to one another, this manner of scanning can be called "x-y" or "Cartesian scanning" and the coordinates of the detected particles are Cartesian coordinates. Such an x-y scanning is known in the art and is described e.g. in U.S. Pat. No. 5,699,447.

In a preferred embodiment, the aforesaid sensor comprises a collector for collecting the scattered light reflected by the wafer in at least one direction, means for separating the collected light into two components having the wavelengths of the two laser beams and photo-electric means for generating electric analog signals representing said components; and the A/D converter samples said electric analog signals at a predetermined frequency and converts them to digital signals.

The laser source may comprise two laser diodes, which emit the two laser beams having different wavelengths, or it may comprise a single laser diode and a non-linear crystal whereby to obtain two different wavelengths. The two laser beams may have the same parameters, except for the difference in wavelength, or may have different parameters, which can easily be taken into account when the signals representing their reflections from the wafer surface are compared.

When a turntable is used, the association to each detected particle of its coordinates on the wafer can be carried out as described in the aforesaid copending application. In each machine, the equations representing the It rotary motion of the wafer axis and the variation of the distance of the spot of the beams from the wafer center locate the detected particle in a polar coordinate system; and this latter can be easily transformed to a Cartesian coordinate system defined by the geometry of the die arrangement on the wafer.

It will be understood, therefore, that the apparatus of this invention can be combined with that of the copending application. In such a combined apparatus, not only the mechanical means for supporting and shifting the wafer are common, but the analysis of the pattern wafer surface or other surface by the method of the said copending application and the detection of foreign, small particles by the method of this application, which comprises the analysis of the digital signals representing the light scattered by the wafer, can be carried out at least in part by the same hardware and/or software means. This invention, therefore, comprises such a combined apparatus.

DETAILED DESCRIPTION OF PREFERRED EMBODIMENTS

The preferred embodiments are directed to the analysis of a patterned or bare surface of a semiconductor wafer, but it must be understood that this is done for purposes of illustration only, and that the invention can be applied to the analysis of any surface.

The scattering that results from the illuminated pattern on the wafer is different in nature from the one that results from a small particle. The signal from the pattern is due to diffraction from edges and corners of the pattern lines. If the pattern is repetitive (like in memory cells), then the scattered intensity is the result of interference between all the diffraction sources within the spot. The interference intensity pattern that is received and detected by a large aperture fiber bundle is not sensitive to small fluctuations in the illuminating wavelength. The intensity pattern as a function of wavelength is given by (one dimension approximation):

$$I = Ca^2 \left[\frac{\sin(qa)}{qa}\right]^2 \left[\frac{\sin(Nqa)}{\sin(qd)}\right]^2 \quad q = \frac{2\pi\sin\theta}{\lambda}$$

Where C is a constant, $2a$ is the width of a single line, d is the separation between the lines, N is the number of lines which the spot covers in one direction, $\lambda$ is the illumination wavelength and $\theta$ is the elevation angle measured from the zero order reflected beam direction. Simulation made to study the behavior of the above equation shows that by integrating the intensity in the range $\theta=2-10°$ (as the fiber bundle does) and using N=5–10, one gets no more than a 2% difference in intensity by changing the illumination wavelength from 630 nm to 670 nm.

On the other hand, the scattered intensity resulted from a very small particle ($d<<\lambda$ where d is the particle radius), lying on the same area of the wafer and illuminated by the same laser beam, is given by:

$$I_s \propto \frac{d^6}{\lambda^4}$$

Where $I_s$ is the scattering intensity in some direction in space. By differentiating the intensity with respect to the wavelength, one finds that a change in 1% in the wavelength brings to a change of 4% in the intensity. That means that we can expect to get a 20% difference in scattered intensity from the particle on the wafer by changing the illumination wavelength from 630 nm to 670 nm.

Figure 1:
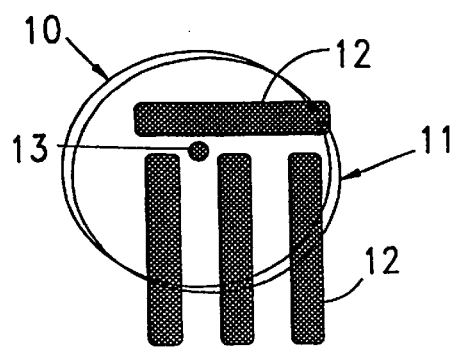
FIG. 1 schematically illustrates the laser footprints on a wafer surface according to a first embodiment of the invention.

FIG. 1 schematically illustrates the formation of the illuminating laser beam footprints or spots in a first embodiment of the invention, in which said two laser beams, having different wavelengths $\lambda_1$ and $\lambda_2$, generate overlapping footprints or spots on the surface to be checked for the presence of small particles. In FIG. 1, numeral 10 designates the spot generated by the light source with wavelength $\lambda_1$. Numeral 11 designates the light spot generated by the laser beam of wavelength $\lambda_2$. 12 indicates pattern lines of the wafer under examination. For purposes of illustration, the two light spots are shown as not completely overlapping, but in practice they could and desirably should be completely overlapping. Number 13 designates a small particle, the dimensions of which are considerably smaller than the wavelength of the two laser beams. Apart from the differences in wavelengths, all the parameters of two illuminating lasers are identical. In this example, the $\lambda_1$ is 630 nm and $\lambda_2$ is 670 nm.

Figure 2A:
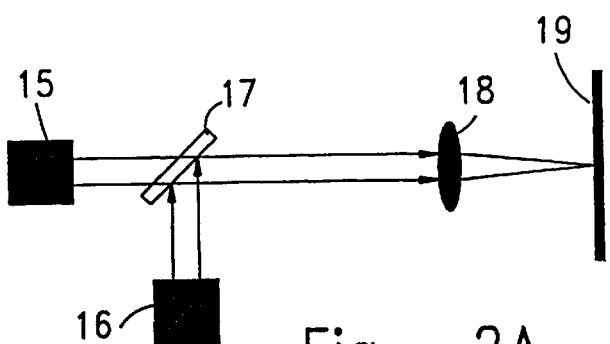
FIG. 2a is a schematic illustration of the generation of the laser beams by two laser diodes and of their focusing on the wafer.

FIG. 2a shows how the two laser beams are generated according to an embodiment of the invention and are concentrated on the wafer surface under examination. 15 indicates a diode laser generating a beam of 630 nm and 16 designates a diode beam generating a beam of 670 nm. The two beams are directed onto the dichroic beam splitter 17, which directs them to focusing lens 18. The beam splitter could be substituted by other beam deviating means and the lens could be substituted by other focusing means, e.g. more complex optical components. Lens 18 concentrates the two beams on the surface of wafer 19, to produce the two overlapping spots illustrated in FIG. 1.

Figure 2B:
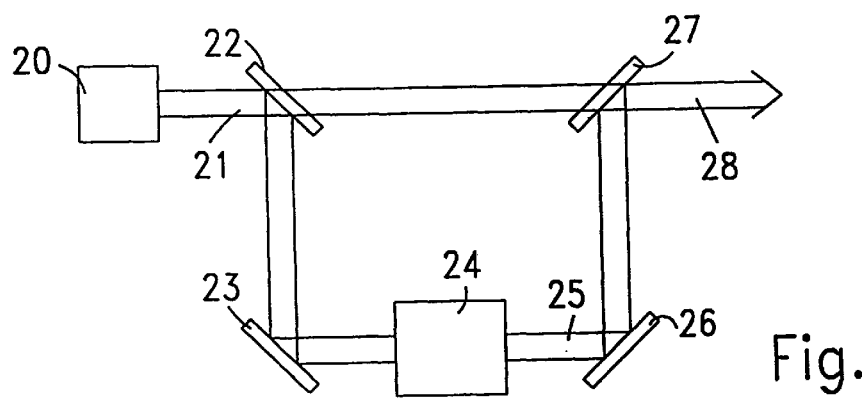
FIG. 2b is a schematic illustration of the generation of the laser beams by a single laser diode and a non-linear crystal.

FIG. 2b shows how the two laser beams are generated according to another embodiment of the invention. Numeral 20 indicates a laser diode. The beam 21 generated by it, having a first desired wavelength, is directed onto a dichroic beam splitter 22, which produces a beam directed to mirror 23. Said mirror directed reflects said beam to a non-linear crystal 24, from which emerges a beam 25 having the second desired wavelength. Beam 25 is reflected by mirror 26 to another dichroic beam splitter 27, by which it is united to the beam that has passed through beam splitter 22 and has the first wavelength, to form a composite beam 28. Beam 28 is focused onto the wafer as shown in FIG. 2a.

Figure 3:
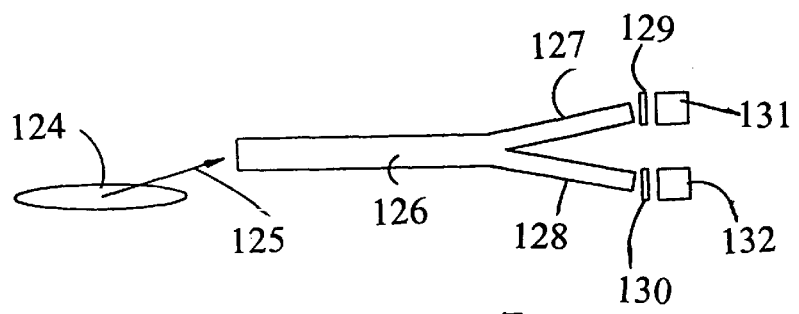
FIG. 3 is a schematic illustration of the collection and separation of the scattered beams according to an embodiment of the invention.

The scattered light is analyzed as schematically illustrated in FIG. 3. Numeral 124 designates, once again, the wafer. At any given moment, a specific pixel of the wafer scatters the light, as indicated by arrow 125, and scattered light is collected by optical fiber bundle 126, which is divided into two branches, 127 and 128. 129 and 130 are two edge type filters, the first of which passes the light of the wavelength $\lambda_1$ and does not pass the light having wavelength $\lambda_2$, while the other one passes wavelength $\lambda_2$ and not wavelength $\lambda_1$. The scattered light of wavelength $\lambda_1$ is then detected by a detector 131, while the light of wavelength $\lambda_2$ is detected by a detector 32. Detectors 131 and 132 produce analog electrical signals, which are then sampled, and the samples are conveyed to comparing means, which may be hardware or software means.

Figure 4:
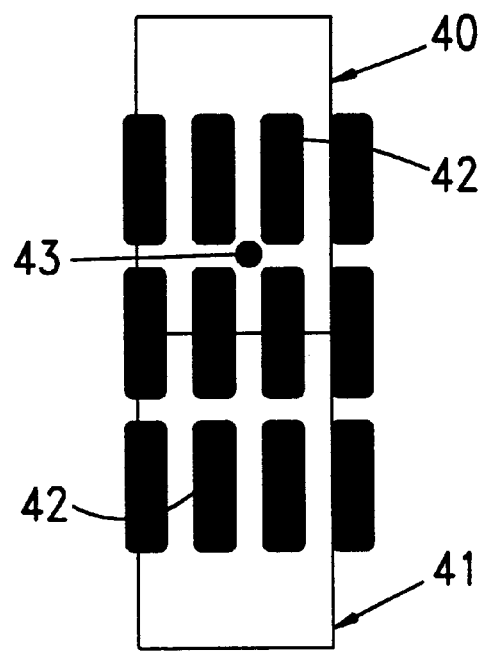
FIG. 4 schematically illustrates the laser footprints on a wafer surface according to a second embodiment of the invention.

The pattern lines 12 of the wafer will produce a difference in intensity of the signals outputted by detectors 131 and 132, even if there is no small particle such as particle 13. Scatter signals that result from the illuminated pattern of a wafer are different from those which result from a small particle. The scatter signal of the pattern is due to diffraction from edges and corners of the pattern lines. If the pattern is repetitive (as in memory cells), the scattered intensities result from interference between all the diffraction sources within the footprint or spot of the laser beams on the wafer. The interference intensity pattern that is received and detected by a large aperture fiber bundle is not sensitive to small fluctuations in the illuminating wavelength. For instance, a change in the illumination wavelength of 630 nm to 670 nm will cause no more than a 2% difference in intensity of the scatter signal. On the other hand, the scatter signal intensity due to a very small particle, lying on the same area of the wafer and illuminated by the same laser beam, is much more sensitive to the laser wavelength. For example, a change of 1% in the wavelength will bring a change of 4% in the intensity of the scatter signal. Therefore, by using two different wavelengths of 630 nm and 670 nm, as in this example, a difference in the intensity of the light scattered from the particle on the wafer will be found to exceed 20%. Subtracting the output of detector 31 from detector 32 and enhancing the difference by amplifier electronics, one obtains a combined signal that will practically cancel the background noise due to the pattern and will magnify the effective signal-to-noise relation from the particle in the illuminated area. FIG. 4 illustrates another embodiment of the invention, in which two laser beams of wavelengths $\lambda_1$ and $\lambda_2$ are so directed onto the wafer surface as to produce two adjacent, non-overlapping footprints or spots indicated by 40 and 41. 42 represents pattern lines in a periodic area of the wafer, for instance, a memory area. Numeral 43 indicates a small particle. Since the footprints or spots are not superimposed, one could not state in general that the same signal would be expected from the two beams, even if there were no particle on the surface. However, if the surface is smooth or is patterned in uniform manner, such as in memory areas, or if anyway the illuminating spot or footprints of each wavelength is so large as to cover a few tens of pattern lines, it would be expected that the two scatter signals resulting from each of the beams be practically constant, unless one of the beams contains a particle. Therefore, this embodiment differs from the previous one only in the way of focusing the beams on the surface under examination. The analysis of the scatter signals is the same as in the previous case.

Although this invention is directed to the detection of small particles, a variant thereof permits to detect particles of any size on bare or uniformly patterned surfaces. This can be achieved by the embodiment of FIG. 4. If the scanned area is uniform and neither of the two beam spots impinges on a particle, the difference between the two signals received from the two beams should be zero and remains about zero even after amplification. However, if one of the two beams impinges on a particle, the difference signal will be significant and will become very large after amplification. This means that the ratio of signal to noise is almost ideal and one can detect even small changes in signal over zero noise. The opposite would occur if a single wavelength scanning spot were used, in which case small changes in signal would have to be detected over greater noise. The difference between the two methods is very considerable: the use of the two wavelength difference signal as the main signal to be amplified and analyzed, results in the reduction or cancellation of the noise from the inspected surface.

Figure 5:
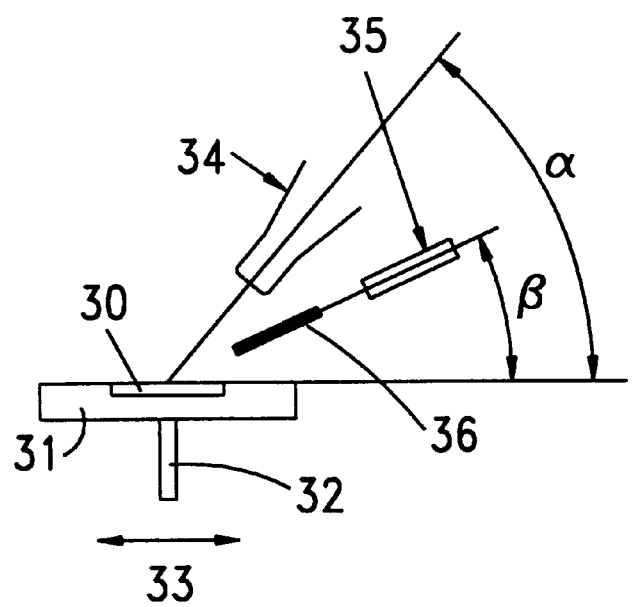
FIG. 5 is a schematic illustration in vertical view of the optical illuminating and collecting components of an apparatus according to an embodiment of the invention.

FIG. 5 schematically illustrate the relationship between the wafer and the optical components in an apparatus according to an embodiment of the invention. Wafer 30 is supported by support disk 31 and rotated by shaft 32 about an axis passing through the center of the wafer. The wafer is shifted parallel to itself, as indicated by arrows 33, by means not shown as they may be conventional. Numeral 34 symbolically indicates the illuminating apparatus of FIG. 2, which, in this embodiment, direct the two laser beams on the wafer surface at an angle $\alpha$. Two laser generators comprised in apparatus 34, and not shown, emit beams of two slightly different wavelengths, which are collected by fiber bundle 36 and processed by collecting device 35, illustrated in FIG. 3 as set at an angle $\beta$ to the wafer surface, to generate two superimposed or adjacent beams, as desired. A plurality of fiber bundles, such as 36, distributed about the wafer in any desired number of directions, could be used, and each one of them would produce two scatter signals, that could be processed as described hereinbefore.

The light collected by optical fiber bundle 36 (or each such bundle, if a plurality are used) is separated into two beams of the two wavelengths, which are transmitted to two photodetectors, all as illustrated in FIG. 3. The output of every photodetector is sampled by a sampler and the output of the samplers is transmitted to hardware and/or software comparing means, not shown.

While embodiments of the invention have been described by way of illustration, it will be apparent that many modifications, variations and adaptations may be made therein by persons skilled in the art, without departing from the spirit of the invention or exceeding the scope of the claims.

What is claimed is:

1. A process for detecting small particles on the outside surface of an object, which comprises:

irradiating an outside surface of the object with two light beams having a small difference in wavelength, the light not passing through the object to reach the surface;

collecting the light that is scattered by the surface in at least one direction;

separating the collected light, by filtering it, into two component beams, each of which has the wavelengths of one of the irradiating beams; and comparing the intensities of the two component beams.

2. A process for detecting small particles on a wafer surface, chosen from among patterned and smooth areas of semiconductor surfaces, which comprises:

irradiating the wafer surface with two light beams having a small difference in wavelength, the light not passing through the wafer to reach the surface;

collecting the light that is scattered by the wafer surface in at least on direction;

separating the collected light, by filtering it, into two component beams, each of which has the wavelengths of one of the irradiating beams; and comparing the intensities of the two component beams.

3. A process according to claim 1, comprising directing the irradiating beams at a slant with respect to the surface.

4. A process according to claim 1, comprising focusing the irradiating light beams so as to superimpose their footprints.

5. A process according to claim 1, comprising focusing the irradiating light beams so as to form adjacent footprints.

6. A process according to claim 1, comprising irradiating the wafer surface with two laser beams having a small difference.

7. A process according to claim 1, comprising collecting the light scattered by the surface by means of optical fibers.

8. A process according to claim 1, comprising separating the collected light in two component beams by filtering it.

9. A process according to claim 1, comprising comparing the intensities of the two component beams by directing each component onto a photodetector, thereby producing two optical signals, transducing each optical signal into an analog electric signal, sampling the resulting two electric signals, thereby obtaining two corresponding digital signal, and feeding said digital signals to a comparator.

10. A process according to claim 1, further comprising amplifying the two component beams.

11. A process according to claim 1, further comprising shaping the two component beams.

12. A process according to claim 6, comprising separately generating the two laser beams and optically processing them to impart on them the desired similar geometry and focus them on the surface so that they have overlapping footprints.

13. A process according to claim 6, wherein separately generating the two laser beams and optically processing them to impart on them the desired similar geometry and focus them on the surface so that they have adjacent footprints.

14. A process according to claim 13, wherein the two laser beams are optically processed by deviating them by means of a beam splitter and focusing them by means of a lens.

15. A process according to claim 1, comprising irradiating the wafer surface with two light beams having a difference in wavelength comprised between 1 and 5% of the average of the two wavelengths.

16. A process according to claim 1, for detecting particles on bare or uniformly patterned wafer surfaces, which comprises irradiating the surface with two light beams having the same parameters, except for a small difference in wavelength, and impinging on said surface in two different, adjacent spots, collecting the light scattered from said two spots to form two collected beams, producing a difference signal representing the difference of the intensities of the said two collected beams, and recognizing the presence of a particle if said difference signal is significant.

17. A process according to claim 16, further comprising amplifying the difference signal.

18. An apparatus for the detection of small particles on surfaces, particularly surfaces of patterned, semiconductor wafers, which comprises:
   a) a stage for supporting a wafer;
   b) laser source and optics for generating at least two laser beams having different wavelengths;
   c) optical components for superimposing said beams and directing them onto the wafer to scan the wafer surface without the light passing througgh the wafer to reach the surface;
   d) a sensor for sensing the scattered light reflected by the wafer and separating it into two components having the wavelengths of said laser beams;
   e) A/D converter for generating digital signals corresponding to said two components; and
   a comparator for analyzing whether said digital signals indicate the presence of small particles.

19. An apparatus according to claim 18, wherein the stage for supporting the wafer is a turntable.

20. An apparatus according to claim 18, wherein the stage for supporting the wafer is a slide.

21. An apparatus according to claim 18, wherein the laser source comprises two laser diodes emitting laser beams having different wavelengths.

22. An apparatus according to claim 18, wherein the laser source comprises a laser diodes emitting a laser beams having a first wavelength and a non- linear crystal receiving a laser beam having said first wavelength and emitting a laser beam having a different wavelength.

23. An apparatus according to claim 22, comprising a laser diode, a first beam splitter, a second beam splitter for receiving a first beam from said first beam splitter, a non-linear crystal, a first mirror for directing a second beam from said first beam splitter to said crystal, and a second mirror for directing the beam issuing from said crystal to said second beam splitter.

24. An apparatus for the detection of small particles on surfaces, particularly patterned or smooth surfaces of semiconductor wafers, which comprises:
   a) a stage for supporting a wafer;
   b) laser source and optics for generating at least two laser beams having different wavelengths;
   c) optical components for directing and focusing said beams onto a surface of the wafer so as to produce thereon spots chosen from among overlapping and adjacent spots, without the light passing through the object to reach the surface;
   d) optical fiber for collecting the scattered light reflected from the surface of the wafer in at least one direction;
   e) a photoelectric circuit for generating electric analog signals representing said components;
   f) an A/D converter for sampling said electric analog signals at a predetermined frequency and converting them into digital signals; and
   g) a comparator for analyzing whether the digital signals thus obtained indicate the presence of small particles.

25. Apparatus according to claim 18, for the detection of particles on bare or uniformly patterned surfaces of semiconductor wafers, wherein the optical components for directing and focusing the beams onto the wafer are such as to produce two different, adjacent spots, and the comparator comprises a signal generator for producing a difference signal representing the difference of the intensity of the two collected beams having different wavelengths.

* * * * *